(12) United States Patent
Min et al.

(10) Patent No.: US 12,374,442 B2
(45) Date of Patent: Jul. 29, 2025

(54) ASSESSMENT OF CORONARY FUNCTION VIA ADVANCED 3D PRINTED MODELS

(71) Applicant: Cornell University, Ithaca, NY (US)

(72) Inventors: James K. Min, Brooklyn, NY (US); Simon Dunham, New York, NY (US); Bobak Mosadegh, New York, NY (US); Kranthi Kumar Kolli, New York, NY (US)

(73) Assignee: Cornell University, Ithaca, NY (US)

( * ) Notice: Subject to any disclaimer, the term of this patent is extended or adjusted under 35 U.S.C. 154(b) by 1325 days.

(21) Appl. No.: 17/046,382

(22) PCT Filed: Apr. 11, 2019

(86) PCT No.: PCT/US2019/027003
§ 371 (c)(1),
(2) Date: Oct. 9, 2020

(87) PCT Pub. No.: WO2019/200108
PCT Pub. Date: Oct. 17, 2019

(65) Prior Publication Data
US 2021/0142886 A1    May 13, 2021

Related U.S. Application Data

(60) Provisional application No. 62/656,285, filed on Apr. 11, 2018.

(51) Int. Cl.
*G16H 30/20* (2018.01)
*A61B 6/50* (2024.01)
(Continued)

(52) U.S. Cl.
CPC .......... *G16H 30/20* (2018.01); *A61B 6/504* (2013.01); *B29C 64/386* (2017.08); *B33Y 50/00* (2014.12);
(Continued)

(58) Field of Classification Search
None
See application file for complete search history.

(56) References Cited

U.S. PATENT DOCUMENTS

| 11,872,085 B2 * | 1/2024 | Vortman | .............. A61B 8/4488 |
| 2004/0236455 A1 * | 11/2004 | Woltman | ................ G06F 30/20 700/132 |

(Continued)

FOREIGN PATENT DOCUMENTS

| CN | 107316554 A | 11/2017 |
| WO | WO-2016/128965 A2 | 8/2016 |

(Continued)

OTHER PUBLICATIONS

Aycock, et al., "Particle image velocimetry measurements in an anatomical vascular model fabricated using inkjet 30 printing," Experiments in Fluids, 2017, vol. 58, No. 11 (8 pages).
(Continued)

*Primary Examiner* — Helen Zong
(74) *Attorney, Agent, or Firm* — Foley & Lardner LLP

(57) ABSTRACT

The present disclosure describes a system that can enable the prediction of coronary flow without invasive medical procedure. The system can generate physical models that can provide an accurate assessment of coronary mechanics and enable realistic simulation of coronary procedures. The models can enable the hemodynamic measurement of flow through the model and the study of flow dynamics through the model and the biomechanics of the model.

20 Claims, 6 Drawing Sheets

(51) Int. Cl.

| | |
|---|---|
| *B29C 64/386* | (2017.01) |
| *B33Y 50/00* | (2015.01) |
| *B33Y 80/00* | (2015.01) |
| *G01F 9/00* | (2006.01) |
| *G01N 15/08* | (2006.01) |
| *G01N 15/10* | (2024.01) |
| *G01N 15/1409* | (2024.01) |

(52) U.S. Cl.
CPC ............... *B33Y 80/00* (2014.12); *G01F 9/00* (2013.01); *G01N 15/1409* (2024.01); *A61B 6/503* (2013.01); *G01N 2015/0853* (2013.01); *G01N 2015/1027* (2024.01); *G05B 2219/49023* (2013.01)

(56) References Cited

U.S. PATENT DOCUMENTS

| | | | |
|---|---|---|---|
| 2004/0236456 A1* | 11/2004 | Pieper | G06F 30/20 700/132 |
| 2016/0117816 A1 | 4/2016 | Taylor | |
| 2016/0166220 A1 | 6/2016 | Bar-Shalev et al. | |
| 2017/0217102 A1* | 8/2017 | Mansi | G16H 50/50 |

FOREIGN PATENT DOCUMENTS

| | | |
|---|---|---|
| WO | WO-2016/137425 | 9/2016 |
| WO | WO-2018/018033 A1 | 1/2018 |

OTHER PUBLICATIONS

International Search Report and Written Opinion in International Patent Application No. PCT/US2019/027003 dated Jul. 25, 2019.
Sommer, et al., "Design Optimization for Accurate Flow Simulations in 30 Printed Vascular Phantoms Derived from Computed Tomography Angiography," Medical Imaging 2017: Imaging Informatics for Healthcare, Research, and Applications, Feb. 11, 2017, vol. 10138 (26 pages).
Extended European Search Report on EP 19784551.4 DTD Nov. 19, 2021.
Sommer et al., "3D Printed Cardiovascular Patient Specific Phantoms Used for Clinical Validation of a CT-derived FFR Diagnostic Software" Medical Imaging 2018: Biomedical Applications in Molecular, Structural, and Functional Imaging. Feb. 2018, vol. 10578 (22 pages).
Vukicevic et al., "Cardiac 3D Printing and its Future Directions", JACC: Cardiovascular Imaging, Feb. 6, 2017, vol. 10, No. 2 (14 pages).

* cited by examiner

ASSESSMENT OF CORONARY FUNCTION VIA ADVANCED 3D PRINTED MODELS

CROSS-REFERENCE TO RELATED APPLICATION

This application is a U.S. National Stage Application under 35 U.S.C. § 371 of International Patent Application No. PCT/US2019/027003, filed on Apr. 11, 2019, which claims priority to U.S. Provisional Patent Application No. 62/656,285 filed on Apr. 11, 2018, each of which is herein incorporated by reference in its entirety for all purposed.

BACKGROUND OF THE DISCLOSURE

Coronary artery disease (CAD) is a large cause of patient morbidity and mortality. In the United States, CAD affects more than 16 million adults, accounts for more than ⅓ of deaths, and is responsible for more than 1.2 million hospitalizations annually. Despite medical therapy, coronary revascularization is required for more than 1.5 million individuals annually. For stable individuals with complex multivessel disease, a coronary artery bypass graft (CABG) remains the mainstay of treatment for myocardial ischemia reduction and is performed for nearly 400,000 individuals in the U.S. annually.

SUMMARY OF THE DISCLOSURE

The clinical gold standard for evaluation of ischemia can be invasive fractional flow reserve (FFR). In this procedure, a minimally invasive pressure wire can be used to measure the pressure drop from the aortic root (Pa) to a segment of the coronary branches distal (Pd) to an atherosclerotic lesion of interest. This method has proven to have significant prognostic utility; however, it can have several limitations. For example, the method may only evaluate the significance of epicardial CAD and does not consider the effect of the microcirculatory resistance or related disorders. Also, the method can evaluate the trans-lesional pressure differences at hyperemia wherein maximal microvascular vasodilation has been achieved by administration of adenosine, and thus cannot consider patient-specific ischemic thresholds for individuals who may never achieve maximum flow during normal daily activities. Also, the method considers only a single hemodynamic index averaged across time and does not provide other potentially important coronary hemodynamic information, such as time-varying local blood flow patterns and the effects of strains acting upon a plaque. The method also does not consider other CAD features that may present a risk of myocardial infarction (MI).

Computational fluid dynamics (CFD) can provide a non-invasive alternative to FFR. FFR can provide some ability to explore the effects of subtle hemodynamic effects and to predict the effect of flow and microcirculatory resistance. However, this method can be limited due to many of the assumptions associated with CFD, particularly rigid wall mechanics. Even more advanced simulations that incorporate fluid/solid interactions (FSI) must make numerous assumptions and approximations that are difficult to validate experimentally. Furthermore, these methods can be computationally prohibitive.

The present disclosure describes an alternative approach whereby in vitro benchtop coronary models are fabricated using 3D printed (also referred to as additive manufacturing) models generated from coronary CT angiography (CCTA). By using advanced 3D printing methods, the system provides models, which provide realistic tissue mechanics (from flexible digital material printing). The models can be used with flow loops with adjustable flow profiles (programmable pulsatile flow pump) and microcirculatory resistance (needle valve and capacitive chamber). By printing these models from transparent materials, the system enables the measurement of hemodynamics and biomechanics using particle imaging velocimetry (PIV) and TOMO-PIV. The system can also enable additional biomechanics to be measured by incorporating flexible strain sensors directly into the 3D print model. The models can have attributes that include realistic tissue properties and transparent, which can enable the models to provide meaningful prognostic utility: These models can provide the ability to predict FFR non-invasively while accounting for fluid/solid interactions and considering factors such as flow and microcirculation. Many of the hemodynamic and biomechanical features that can be evaluated (wall shear stress, particle resonance time, etc.) have the potential to provide significant additional predictive value for MI. Furthermore, these models can be used to test various coronary interventions and predict the local tissue stresses and changes in hemodynamics associated with a particular intervention.

According to at least one aspect of the disclosure, a method can include receiving at least one image of a target anatomy of a subject. The method can include generating an anatomy geometry of the target anatomy based on segmenting the at least one image of the target anatomy. The method can include generating a density profile based on the anatomy geometry and a mapping between voxel values of the at least one image of the target anatomy and a deformation value of the target anatomy. The method can include generating a physical model of the target anatomy based on the anatomy geometry and the density profile. The method can include measuring a value of the physical model or a fluid as the fluid flows through the physical model.

In some implementations, the fluid can include a plurality of particles and the method can include determining a displacement of the plurality of particles between a first time point and a second time point. The method can include determining a flow rate based on the displacement of the plurality of particles between the first time point and the second time point. The method can include identifying a vorticity within the fluid based on the displacement of the plurality of particles between the first time point and the second time point. The valuecan include an energy loss, a particle residence, a pressure within the physical model, or a strain of the physical model.

The physical model can include an electrode on a first face of a wall of the physical model and the fluid comprises a salt solution. The method can include measuring a capacitance of the wall between the electrode on the first face of the wall and the fluid. The method can include embedding a plurality of particles within at least one wall of the physical model. The method can include determining a displacement of the plurality of particles between a first time point and a second time point. The method can include determining a strain of the at least one wall based on the displacement of the plurality of particles.

The fluid can include a first plurality of particles and the physical model can include a second plurality of particles embedded within at least one wall of the physical model. The method can include illuminating the first plurality of particles with a first wavelength of light and illuminating the second plurality of particles with a second wavelength of light. The density profile comprises, for each layer of the anatomy geometry, a dither pattern indicating a material ratio.

According to at least one aspect of the disclosure, a system can include one or more processors and a memory storing processor executable instructions. The system can receive at least one image of a target anatomy of a subject. The system can generate an anatomy geometry of the target anatomy based on segmenting the at least one image of the target anatomy. The system can determine a density profile based on the anatomy geometry and a mapping between voxel values of the at least one image of the target anatomy and a deformation value of the target anatomy. The system can transmit to a three-dimensional printer a data structure including the anatomy geometry and the density profile to manufacture a physical model of the target anatomy. The system can measure a value of the physical model or a fluid as the fluid flows through the physical model.

In some implementations, the fluid can include a plurality of particles and the system can determine a displacement of the plurality of particles between a first time point and a second time point. The system can determine a flow rate based on the displacement of the plurality of particles between the first time point and the second time point. The system can identify a vorticity within the fluid based on the displacement of the plurality of particles between the first time point and the second time point.

In some implementations, the value can include an energy loss, a particle residence, a pressure within the physical model, or a strain of the physical model. The physical model can include an electrode on a first face of a wall of the physical model and the fluid comprises a salt solution. The system can determine a capacitance of the wall between the electrode on the first face of the wall and the fluid. The system can determine a displacement of a plurality of particles embedded within at least one wall of the physical model between a first time point and a second time point. The system can determine a strain of the at least one wall based on the displacement of the plurality of particles. The system can include a laser to generate a first wavelength of light to illuminate a first plurality of particles and generate a second wavelength of light to illuminate a second plurality of particles with a second wavelength of light. The density profile comprises, for each layer of the anatomy geometry, a dither pattern indicating a material ratio.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a system that can enable the prediction of coronary flow without invasive medical procedure. The system can generate physical models that can provide an accurate assessment of coronary mechanics and enable realistic simulation of coronary procedures. The models can enable the hemodynamic measurement of flow through the model and the study of flow dynamics through the model and the biomechanics of the model.

Figure 1:
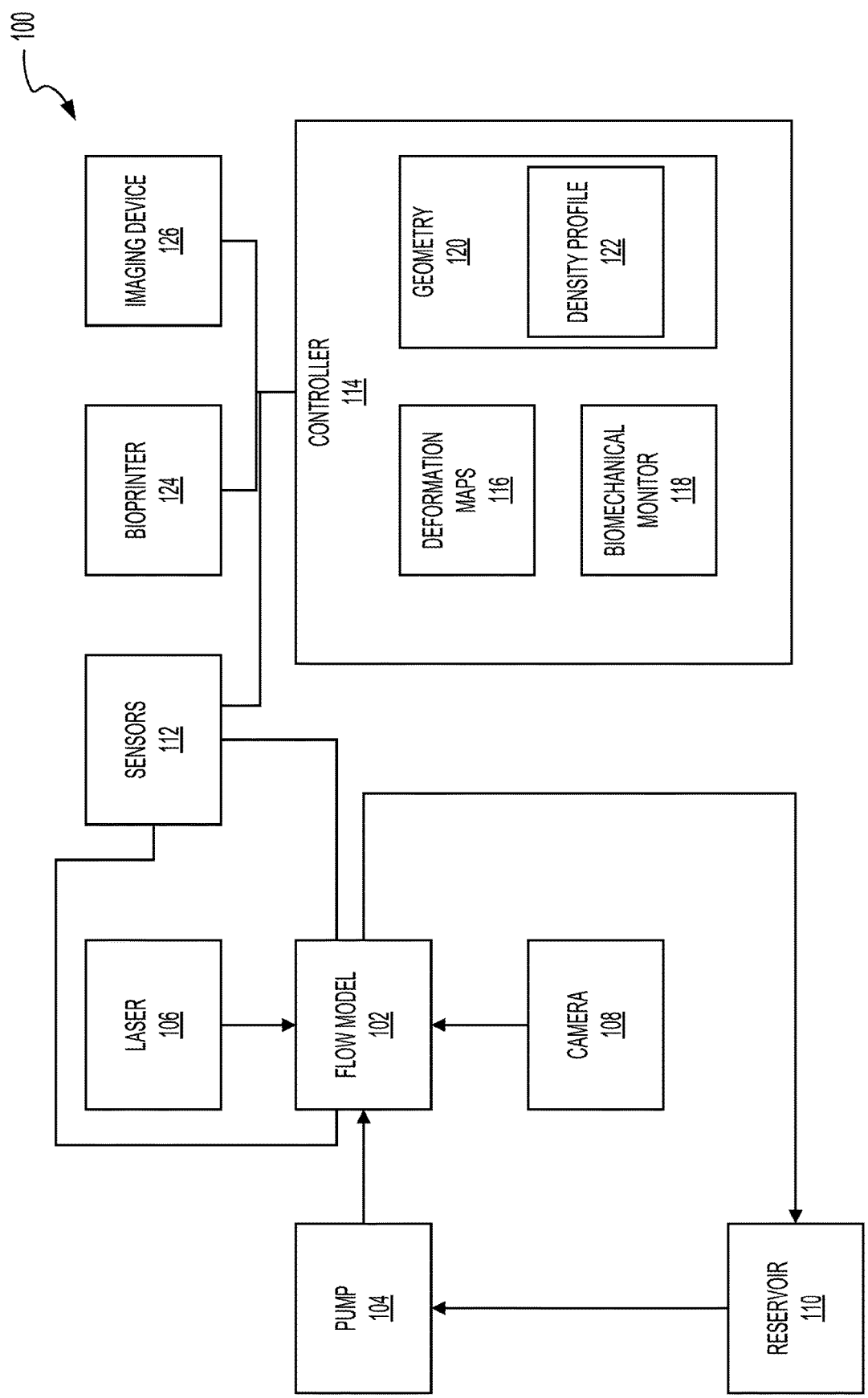
FIG. 1 illustrates a block diagram of an example system to model and measure biomechanical properties of a target anatomy.

FIG. 1 illustrates a block diagram of an example system 100 to model and measure biomechanical properties of a target anatomy. The system 100 can include a physical model 102 of which the biomechanical properties are measured. The one or more pumps 104 can flow a fluid through the physical model 102. Fluid flow and other biomechanical properties of the physical model 102 can be measured by lasers 106, cameras 108, and sensors 112. The physical model 102 can be generated by a bioprinter 124 based on one or more images of the in vivo target anatomy captured by one or more imaging devices 126. One or more components of the system 100 can be controlled by the controller 114. The controller 114 can include deformation maps 116 and a biomechanical monitor 118. The controller 114 can generate one or more geometries 120 for printing the physical model 102 by the bioprinter 124. The geometries 120 can each include density profiles 122.

The system 100 can include a physical model 102. The physical model 102 can be a 3D printed, physical model of target anatomy. The target anatomy can be circulatory anatomy of a subject, such as a subject's coronary artery or other vasculature. The physical model 102 is further described in relation to the bioprinter 124 and FIGS. 2-4, among others. The system 100 can generate the physical model 102 based on data such as CT image scans and other imaging data, medical history, and physiological information for a given subject. The physical model 102 can be a patient-specific model of the target anatomy (e.g., the coronary arteries) and can include anatomically-realistic material properties. For example, the system 100 can systematically and comprehensively characterize tissue mechanics of the target tissue and related tissue (e.g., atherosclerotic plaque) and fabricate the physical model 102 to have matching geometry and mechanical properties. The system 100 can receive imaging data from, for example, the imaging device 126 and correlate the image data with tissue densities of the target anatomy.

The system 100 can include one or more pumps 104 to flow fluid through the physical model 102. The pumps 104 can be a pulsatile flow pump. The pumps 104 can be configured to output flows with different pressures, flow rates, and waveforms. The pump 104 can pump a fluid through the physical model 102 that includes particles. In some implementations, the physical model 102 can be printed from an opaque or clear material such that the particles can be imaged by the laser 106 and the camera 108. For example, the laser 106 can illuminate the particles and their movement through the physical model 102 can be captured by the camera 108. As described further below, the controller 114 can capture the movement of the particles through the physical model 102 and can determine, for example, flow patterns, local velocities, and tortuosity based on the movement of the particles. The fluid can exit the physical model 102 and can be captured in the reservoir 110. In some implementations, the pump 104 can recirculate the fluid from the reservoir 110 back through the physical model 102.

The system 100 can include one or more lasers 106 and cameras 108. The camera can be a high-speed camera that can capture the movement of the particles as they flow through the physical model 102. The laser 106 can be a green laser (Raypower 2000 laser, wavelength=532 nm) that can be focused into a planar sheet of light. The laser 106 can illuminate a region of interest (ROI) in the physical model 102. The camera 108 can be a high-speed camera, such as the SpeedSense M110 by Dantec Dynamics. By monitoring particle motion in the ROIs, the controller 114 can determine particle resonance time, turbulence, and reattachment length. The controller 114 can also calculate velocity gradients, shear strain rate, and identify recirculation zones based on the movement of the particles. For an example, where the target anatomy is the coronary artery, the ROIs can include (1) a location about 3 diameters-length proximal of the stenosis, (2) at the stenosis region, and (3) about 6 diameters-length distal to the stenosis.

The system 100 can include one or more sensors 112. The system 100 can include one or more sensors 112 within the flow circuit flowing from the pump 104, through the physical model 102 and to the reservoir 110. For example, the system 100 can include flow and pressure sensors at the inlet of the physical model 102 that can measure the flow rate and the pressure of the fluid flowing into the physical model 102. The system 100 can include sensors 112 (e.g., flow and pressure sensors) within the portion of the fluid circuit running through the physical model 102. The system 100 can include flow and pressure sensors at the outlet of the physical model 102 that can measure the flow rate and the pressure of the fluid flowing out of the physical model 102. The system 100 can include one or more sensors 112 embedded within the physical model 102 or configured to measure properties of the physical model 102. The physical model 102 can include flexible strain sensors that are directly incorporated into the physical model 102 to measure the strain of the physical model 102 as fluid flows through the physical model 102.

For example, because the physical model 102 can recapitulate realistic tissue mechanics, it is possible to measure the stresses applied to and deformations of the physical model 102 to realize greater insight into coronary physiology. In some implementations, the sensors 112 can be sensors that measure the change in capacitance of the walls of the physical model 102. For example, the sensors 112 can measure the changes in the capacitance of dielectric layer sandwiched between two conducting mediums. For these sensors 112, the fluid can include a highly concentrated salt solution that the pump 104 can perfuse through the physical model 102. A wall of the physical model 102 can act as the dielectric layer (whose deformations are being measured). The physical model 102 can include a conductive hydrogel electrode on top of the dielectric layer (e.g., the wall of the physical model 102), and the capacitance of the circuit can be measured. This is described further in relation to FIGS. 3 and 4. As the wall of the physical model 102 stretches, the wall can thin, and the change in capacitance can be measured.

The system 100 can include one or more imaging devices 126. The imaging devices 126 can be medical imaging devices to capture two-dimensional (2D) or three-dimensional (3D) images of the subject's target anatomy. The imaging device 126 can be a computer tomography device. For example, the imaging device 126 can be a coronary CT angiography (CCTA) device.

The system 100 can include one or more controllers 114. The controller 114 can include one or more processors. The processors can provide information processing capabilities to the controller 114. The processors can include one or more of digital processors or digital circuits to process information. Each processor can include a plurality of processing units or processing cores. The processor can be electrically coupled with a memory and can execute or store deformation maps 116, the biomechanical monitor 118, the geometries 120, and the density profiles 122. The controller 114 can include one or more microprocessors, application-specific integrated circuits (ASIC), field-programmable gate arrays (FPGA), or combinations thereof The controller 114 can include a biomechanical monitor 118. The biomechanical monitor 118 can receive signals from the sensors 112 and the camera 108 to monitor the biomechanics of the physical model 102 as fluid flows through the physical model 102. For example, the biomechanical monitor 118 can determine or calculate the fluid flow through and the pressures within the physical model 102. The biomechanical monitor 118 can measure and determine the strain of the walls of the physical model 102.

The biomechanical monitor 118 can perform particle imaging velocimetry (PIV) and tomographic (TOMO)-PIV to measure the hemodynamics and biomechanics of the physical model 102. For example, the camera 108 can capture a plurality of images as the particles flow through the physical model 102. The laser 106 can illuminate the particles as the particles flow through the physical model 102. As described herein, the physical model 102 (or portions thereof) can be transparent to enable the camera 108 to image within an interior volume of the physical model 102. The biomechanical monitor 118 can perform a temporal minimum intensity subtraction at each pixel location of the captured images to remove background illumination. The biomechanical monitor 118 can perform ensemble correlation, dynamic range enhancement, and phase correlations to increase signal-to-noise ratios and measurement accuracy, and to resolve flow regions with large velocity ranges and gradients. The biomechanical monitor 118, using the PIV processing, can calculate wall shear stress values estimated from the velocity fields by determining the near wall velocity gradients. The biomechanical monitor 118 can, using the velocity fields identified through PIV, calculate the vorticity, energy loss, and particle residence time and the pump 104 pumps fluid through the physical model 102.

The biomechanical monitor 118 can perform tomo-PIV to measure the strain in solids by tracking the in-plane displacement of fluorescently tagged particles distributed or embedded within the material of the physical model 102. The laser 106 can illuminate the tracer particles immersed in the material of the physical model 102. The camera 108 can image the scattered light pattern at subsequent times (e.g., time 1 and time 2). The biomechanical monitor 118 can reconstruct the placement of the particles and determine the displacements of the center points of each interrogation voxel containing the particles between the two subsequent times. The biomechanical monitor 118 can determine a strain based on the determined displacement of the particles. In some implementations, the particles embedded within the physical model 102 and the particles flowing within the fluid pumped through the physical model 102 can be activated by different wavelength fluorescence. For example, the laser 106 can generate a first output wavelength to activate the particles embedded within the physical model 102 and a second output wavelength to activate the particles flowing through the fluid.

The controller 114 can generate a geometry 120 for a subject's target anatomy. The geometry 120 can be a data structure for printing the physical model 102 via the bioprinter 124. For example, the geometry 120 can be a file stored in a STL file format or other file format suitable for storing instructions for printing a physical model 102. The geometry 120 can include a density profile 122. In some implementations, the physical model 102 can be printed with different materials that include different physical properties. The density profile 122 can indicate, for each layer of the physical model 102, the distribution of the different materials within the layer of the physical model 102. The controller 114 can generate the density profiles 122 based on deformation maps 116 that can correlate that pixel or voxel values of images from the imaging device 126 to mechanical properties of the subject's in vivo target anatomy.

The deformation map 116 can map the images of a target anatomy to the tissue mechanics of the target anatomy (e.g., coronary arteries and atherosclerotic plaque) such that, from the images from the imaging device 126, the physical model 102 can be fabricated with geometry and mechanical properties that match the subject's target anatomy. Experimental target anatomies can be harvested from, for example, cadavers or animal models, imaged and then mechanically tested to generate the deformation maps 116 which enable the geometry 120 and the density profile 122 to be generated for a subject based on only the image data captured by the imaging device 126. For example, arteries can be attached to a pulsatile bioreactor and subjected to prescribed physiologically realistic conditions. The dilation and physical properties of the harvested target anatomy can be measured as the target anatomy is exposed to, for example, the pulsatile flow conditions. The controller 114 can correlate the measured physical properties to the CT images to create the deformation maps 116 which can include a library of tissue types and corresponding mechanical responses.

As one example of the target anatomy and the generation of the deformation maps 116, the target anatomy can be the coronary artery. For accurate material characterization of human coronary tissue, the system 100 can perform evaluations in the immediate post-mortem period. For example, coronary samples can be from decedents (e.g., 40 decedents) as soon as is possible in the post-mortem period in order to: (1) evaluate tissue mechanical properties, and (2) relate CT image appearances to histopathology. The process can include determining the unstrained length of the Coronary tissue (in-situ). The controller 114 can calculate a natural stretch ratio of the coronaries of interest to estimate the mechanical loading conditions during a biaxial testing protocol. Before mechanical testing by inflation testing, the frozen samples can be slowly thawed at 4° C., then prepared to room temperature 20° C., and placed in phosphate buffered saline (PBS activity of 0.37 MBq/mL) for storage. Samples can be imaged using a CT scanner (GE Revolution, Waukesha, Wis.).

For mechanical testing, multiple coronary artery samples can be harvested per patient with the left main, LAD and LCx artery as one specimen, and the RCA as the second specimen. The specimens can be harvested after CT imaging. The coronary specimens can be isolated from surrounding myocardium and cleared of connective tissue, and snap-frozen in liquid nitrogen for storage in order to minimize decomposition and loss of inherent mechanical properties.

The coronary samples can also undergo histopathology evaluation after CT imaging and mechanical testing. Coronary samples can be processed and cut in paraffin and plastic, cryosectioning, and section grinding. Fixation and co-registration of cross-sections can be performed. For specimen preparation, coronaries can be dissected with large branches. The sections can be stained with hematoxylin and eosin, as well as with Movat pentachrome. Plaque components can be identified.

The cadaveric coronary artery samples can be imaged by CT, with varying CT image acquisition conditions to determine the image variability and coronary arteries and atherosclerotic plaque based upon the acquisition parameters. CT image parameters can vary varying kVp between 80-140 and mA between 400-1000 and employ different iodinated contrast-to-saline to achieve intracoronary opacification between 250-400 HU.

Following imaging, samples can be mounted in a mechanical testing system with an attached bioreactor chamber (Bose BioDynamic 5270, Eden Prairie, Minn.). The test samples can be cannulated within the chamber filled with PBS. Vessels can be tested over a range of physiologic flow conditions (60-200 mmHg, in 10 mmHg increments) and pre-strains ($l_{in-situ}$-1 .2×$l_{in-situ}$). The deformation of coronary arteries during the inflation test can be imaged via a high-resolution camera to create deformation maps of the vessels. Following testing, vessels can be sectioned for opening angle measurements at specified regions of interest (ROI). Under microscopy, flat ring sections in PBS from each ROI under zero-stress configurations can undergo the following measurements: Wall thickness (H), opening angle (a), inner arc length ($L_i$), outer arc length ($L_O$), Area (A), where H=2A/$L_i$+$L_O$ α=π-$L_i$+$L_O$/2H. Under high flow, the regions highlighted show larger dilation locally, indicating their low stiffness, relative to the non-highlighted segments. Each segmented length's stiffness can be determined and correlated to the CT-based densities for that particular segment. In some implementations, the mechanical test methods do not require tissue to be cut from homogeneous regions into individual segments for evaluation on tensile mechanical test fixtures. This can enable for characterization of the entirety of the vessel, thus allowing for direct comparison to volumetric CT images. In parallel, test samples of the formulations of 3D printed materials described above can be characterized to match coronary artery tissue and atherosclerotic plaque. Homogeneous samples of each material ratio can be 3D printed in linear conduits with dimensions comparable to coronaries and tested in the same bioreactor.

Based on these results, mechanics can be characterized and directly compared to coronary samples using the same constitutive model.

To analyze the inflation/extension and deformation data, each arterial specimen can be treated as a non-linear, homogenous and orthotropic body with finite deformation. Deformation in circumferential (θ-axis) and axial (z-axis) directions can be assessed as principle stretches:

$$\lambda_\theta = \frac{\pi}{\pi - a}\frac{r}{R}, \lambda_Z = \frac{l}{L} \tag{1}$$

where 'a' is opening angle, at the zero-stress and loaded states; and 'L' and 'l' the respective lengths.

The corresponding Green strains associated with the above principal stretches are:

$$E_i = 1/2(\lambda_i^2 - 1), i=\theta, z \tag{2}$$

The mean second-Piola Kirchoff stresses, from the experimentally measured data, in the circumferential ($\sigma_{\theta\theta}$) direction can be calculated from Laplace's law and axial ($\sigma_{zz}$) direction can be calculated by enforcing equilibrium and assuming axial force is constant. A Fung type exponential strain energy function can be used as our choice of constitutive model.

The system can correlate the CT image features to mechanical properties. CT images can be reconstructed and co-registered (Advantage Workstation 4.6, GE, Milwaukee, Wis.). Cross-sections from centerline save states can be co-registered to histopathology using distance from ostia, coronary branch points, and cross-sectional diameters, vessel morphology, and plaque components as fiduciary landmarks.

The system can characterize the coronaries and the local properties can be correlated to CT image characteristics and confirmed by histology. The distribution of mechanical properties can be established for coronary artery tissue and atherosclerotic plaque, which can be categorized as low attenuation plaque, fibro-fatty, fibrous, calcified and dense calcified. If distributions are too broad, other patient features (e.g., age, coronary calcium score, etc.) may be used to further discriminate plaques and narrow mechanical property distributions. Once these correlations are determined, a different formulation of 3D print material can be correlated to each tissue type, designed to match the average mechanical response of the tissue type. In some implementations, coronary tissue is non-linear and the 3D print materials can be essentially linear. If no single materials can be used to match the mechanical response of the tissue over the entire range of deformation, the system can perform a least squared analysis across the range of physiologic conditions to determine which linear material can closely match the tissue mechanics over the entire range.

Figure 2:
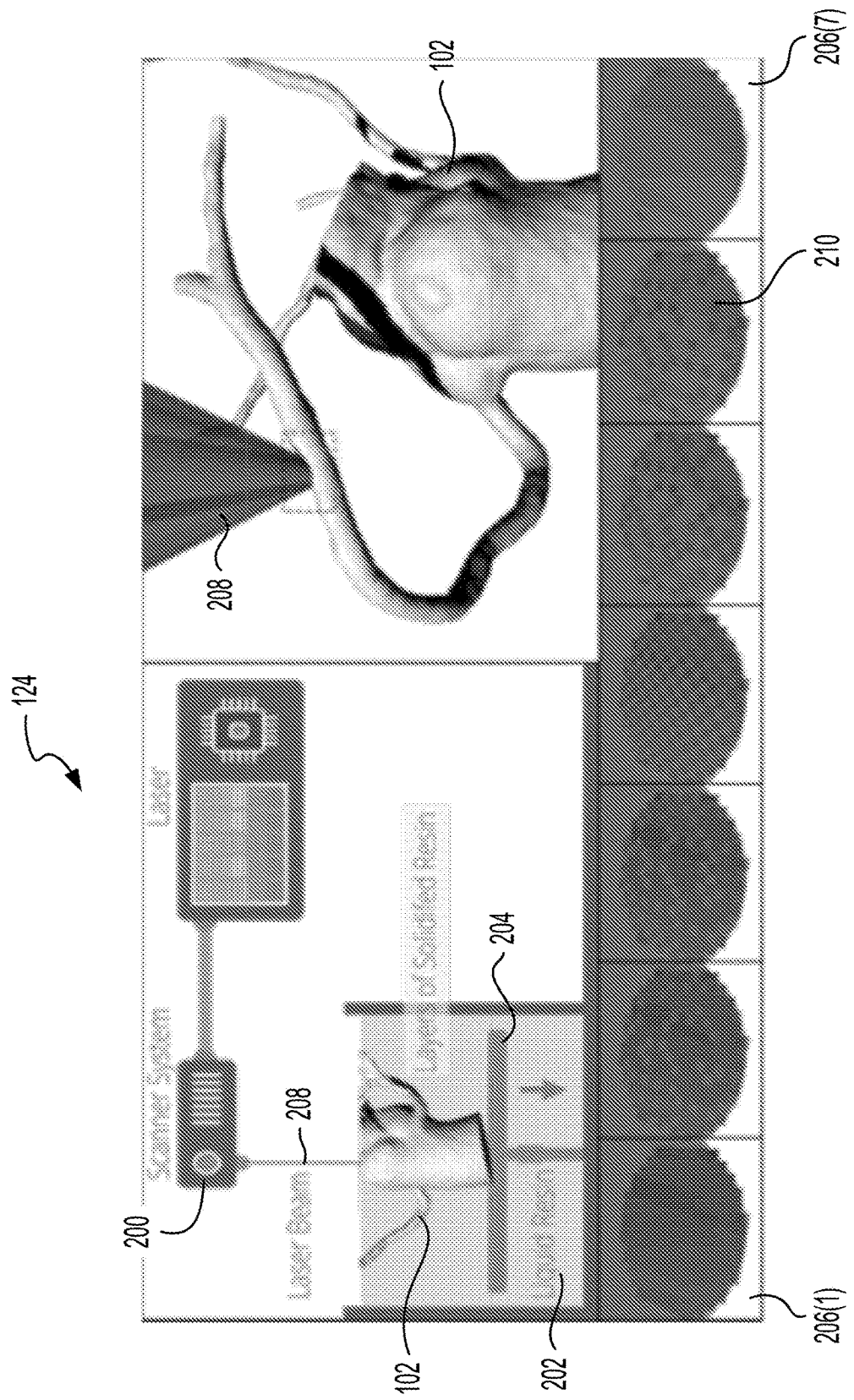
FIG. 2 illustrates an example bioprinter that can be used in the example system illustrated in FIG. 1.

FIG. 2 illustrates an example schematic of the bioprinter 124. The bioprinter 124 can include a scanner system 200 that can include a laser. The bioprinter 124 can include a vat to hold one or more resins 202. The bioprinter 124 can include a platform 204 that is lowered through the resin 202.

The bioprinter 124 can include a vat that can include one or more resins 202. The bioprinter 124 can manufacture transparent, multi-material physical models 102 with soft, tissue-like materials. The resin 202 can be a 2-component, multispectral resin, with 2 different active chemistries. The resin 202 can be a mixture of 2 different chemical moieties: one designed to crosslink and form soft, flexible materials, such as the hydrogels. The second chemical moiety can be a more rigid material chemistry, such as an epoxy. These chemistries can utilize different chemical activation and can be initiated by photoinitiators tuned to different wavelengths of light, which can be generated by the laser of the scanner system 200. As an example, the 2-component resin can include Camphorquinone and triarlysulfonium hexafluoroantimonate. Camphorquinone (CQ) activates around ~450 nm, while triarylsulfonium hexafluoroantimonate salts (CAT2) are initiated at ~360 nm, allowing for independent activation of the two different resins. Because these initiators are free radical and cationic, respectively, the two components can provide chemistry-specific activation. In this way, one wavelength exposure creates a voxel of soft materials, and a second wavelength exposure can create a voxel of rigid material. By creating combined exposures in a similar area with a dither pattern, voxels of mixed materials with intermediate mechanical properties can be achieved. Different mixed dither patterns that result in voxels with stiffnesses can be tuned across a range. Samples with different material ratios can be fabricated in linear conduits and characterized in the same test setup as the coronary specimens. In this way, their mechanics can be characterized using the same constitutive models as for tissue so that specific material ratios can be mapped to specific coronary mechanical properties and CT imaging properties.

The bioprinter 124 can include a scanner system 200. The scanner system 200 can include one or more lasers. The laser can generate the output beam at a plurality of different wavelengths. As described above, the laser generates a light output with a first wavelength to cure a first component of the resin 202 and a light output with a second wavelength to cure a second component of the resin 202. In some implementations, the scanner system 200 can include multiple lasers, which can each output light at a different wavelength. The scanner system 200 can include stepper or other motors to move the laser output within a two-dimensional coordinate system over the platform 204. As illustrated in FIG. 2, the scanner system 200 can output a beam 208 that can cure a top portion of the resin 202. Once the portion of the resin 202 exposed to the beam 208 cures, the platform 204 can lower and a next layer of the physical model 102 can be cured.

FIG. 2 also illustrates a plurality of layers 206(1)-206(7), which can be generally referred to as layers 206, of the physical model 102. Each layer 206 can be defined by the geometry 120 for the physical model 102. Each layer 206 can include a plurality of voxels 210. A voxel 210 can be the smallest three-dimensional volume that can be cured by the laser of the scanner system 200. Each voxel 210 can include one of the cured components of the resin 202. The dithered pattern and the ratio of the voxels that contain each of the different cured resins can determine the physical properties of the layer of the physical model 102. The bioprinter 124 can determine the dithering pattern for a layer based on the deformation maps 116. In some implementations, the multimaterial printing can include polyjet printing or multibath SLA printing.

Figure 3:
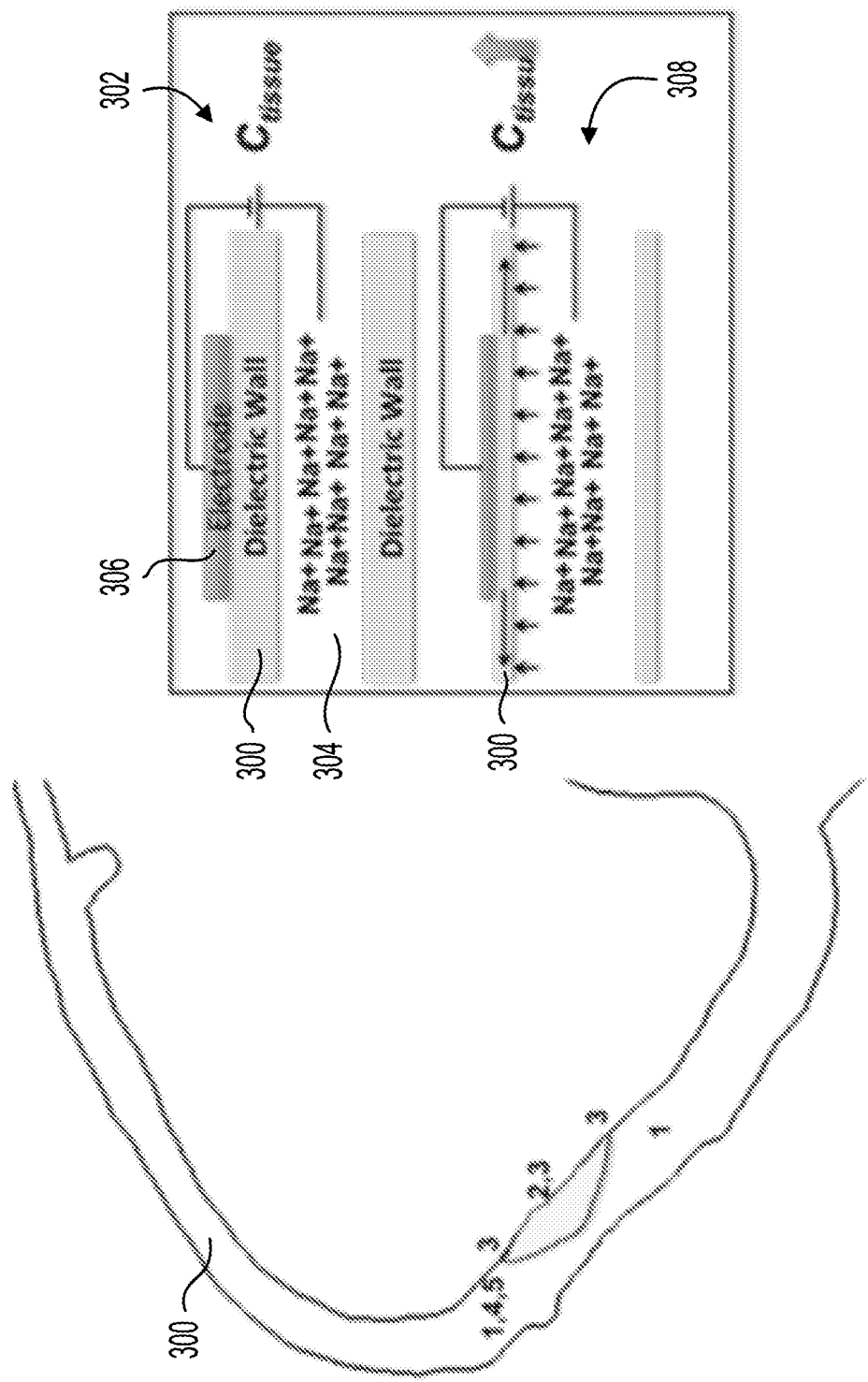
FIG. 3 illustrates a cross-sectional view of a wall of the physical model that can be used with the system illustrated in FIG. 1.
Figure 4:
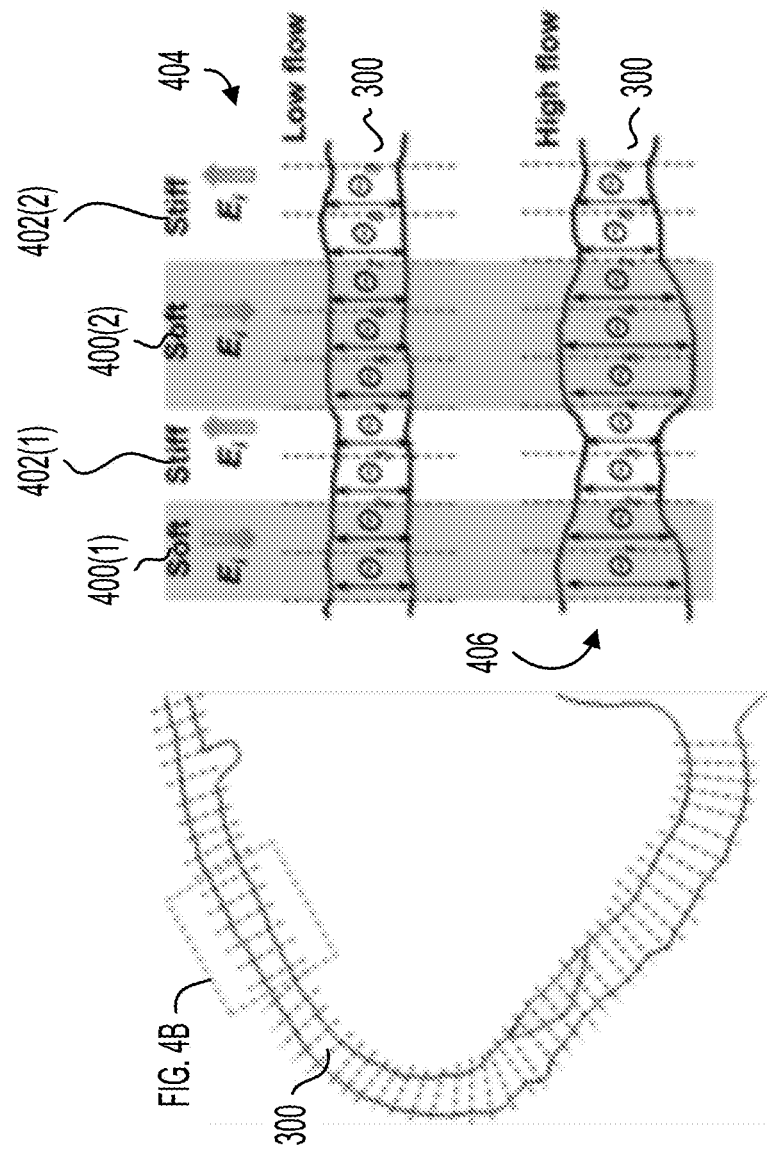
FIG. 4A illustrates a cross-sectional view of the wall of the physical model that can be used with the system illustrated in FIG. 1.
FIG. 4B illustrates an enlarged view of the cross-section of the wall illustrated in FIG. 4A during a low flow state and a high flow state.

FIG. 3 illustrates a cross-sectional view of a wall 300 of the physical model 102. As described above, the wall 300 of the physical model 102 can include a sensor 112. FIG. 3 illustrates a schematic 302 of using the wall 300 as a strain sensor. When using the wall 300 as a strain sensor, the controller 114 can measure the capacitance of the wall 300 between two conducting mediums. A first conducting medium 304 can be a concentrated salt solution within the volume or lumen defined by the wall 300. The first conducting medium 304 can be an electrode. The first conducting medium 304 can come into contact with a first face of the wall 300. The second conducting medium 306 can be a conductive hydrogel electrode 306 (or other electrode) on the outside of the wall 300. The second conducting medium 306 can come into contact with a second face of the wall 300 that is opposite the first face of the wall 300. As the wall 300 stretches, as illustrated in the schematic 308, the wall 300 thins and capacitance of the wall 300 as measured between the first conducting medium 304 and the second conducting medium 306 changes. The sensor can be incorporated into conduits or other regions of interest of the physical model 102.

FIG. 4A illustrates a cross-sectional view of the wall 300 of the physical model 102. FIG. 4B illustrates an enlarged view of the cross-section of the wall 300 during a low flow state and a high flow state. In the example illustrated in FIGS. 4A and 4B, the wall 300 can include a plurality of sections. For example, the wall 300 can include a plurality of first sections 400 and a plurality of second sections 402. The first sections 400 and the second sections 402 can include different mechanical properties. For example, the first sections 400 can be relatively soft and the second sections 402 can be relatively stiff. The first sections 400 and the second sections 402 need not be alternating as illustrated in FIG. 4B. The first sections 400 and the second sections 402 can be of the same length or different lengths. In some implementations, the wall 300 can include a gradual transition between the first sections 400 and the second sections 402. For example, the ratio of the amount of each of the components of the resin in neighboring layers of the wall 300 can gradually change to form a gradual transition between a first section 400 and a second section 402. As illustrated in FIG. 4B, under low flow rates (when the pressure is relatively high), the wall 300 can be compressed. Under high flow rates (when the pressure is relatively low), the soft or complaint portions of the wall (e.g., the first sections 400) can expand in response to the lower external pressure.

Figure 5:
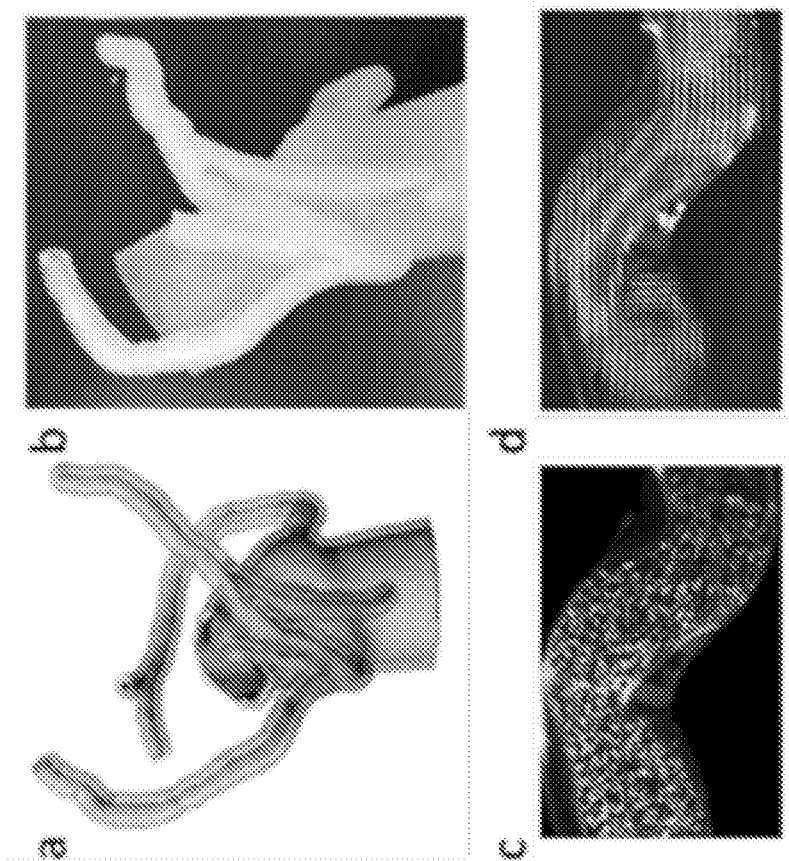
FIGS. 5A-5D illustrate a series of physical models and computational models and the flow analysis through the models.

FIGS. 5A-5D illustrate a series of physical models and computational models and the flow analysis through the models. FIG. 5A illustrates a CAD view of an example physical model 102. FIG. 5B illustrates a manufactured physical model 102. FIG. 5C illustrates fluorescently tagged particles within an example physical model 102. The system can use tomo-PIV to measure the strain in solids by tracking the in-plane displacement of fluorescently tagged particles distributed in a solid. The tracer particles immersed in the material are illuminated by a pulsed light source. The scattered light pattern is recorded using CCD cameras at two subsequent times t and t+Δt. Correspondingly, the 2D projection plane images are transformed into several 1D lines. Making use of the relationship (calibration) between the image (projection) coordinates and the physical space, the particle location in the 2D Tomoplane is then reconstructed from the particles. FIG. 5D illustrates an example 2D tomoplane based on the particles illustrated in FIG. 5C. The displacements of the center points of each interrogation voxel are calculated from two successive images, which can then be used to calculate the associated strains. By using particles with different wavelength fluorescence, strain and flow data can be characterized with the same experimental setup (for PIV), simply by using different wavelength filters on the high-speed camera.

Figure 6:
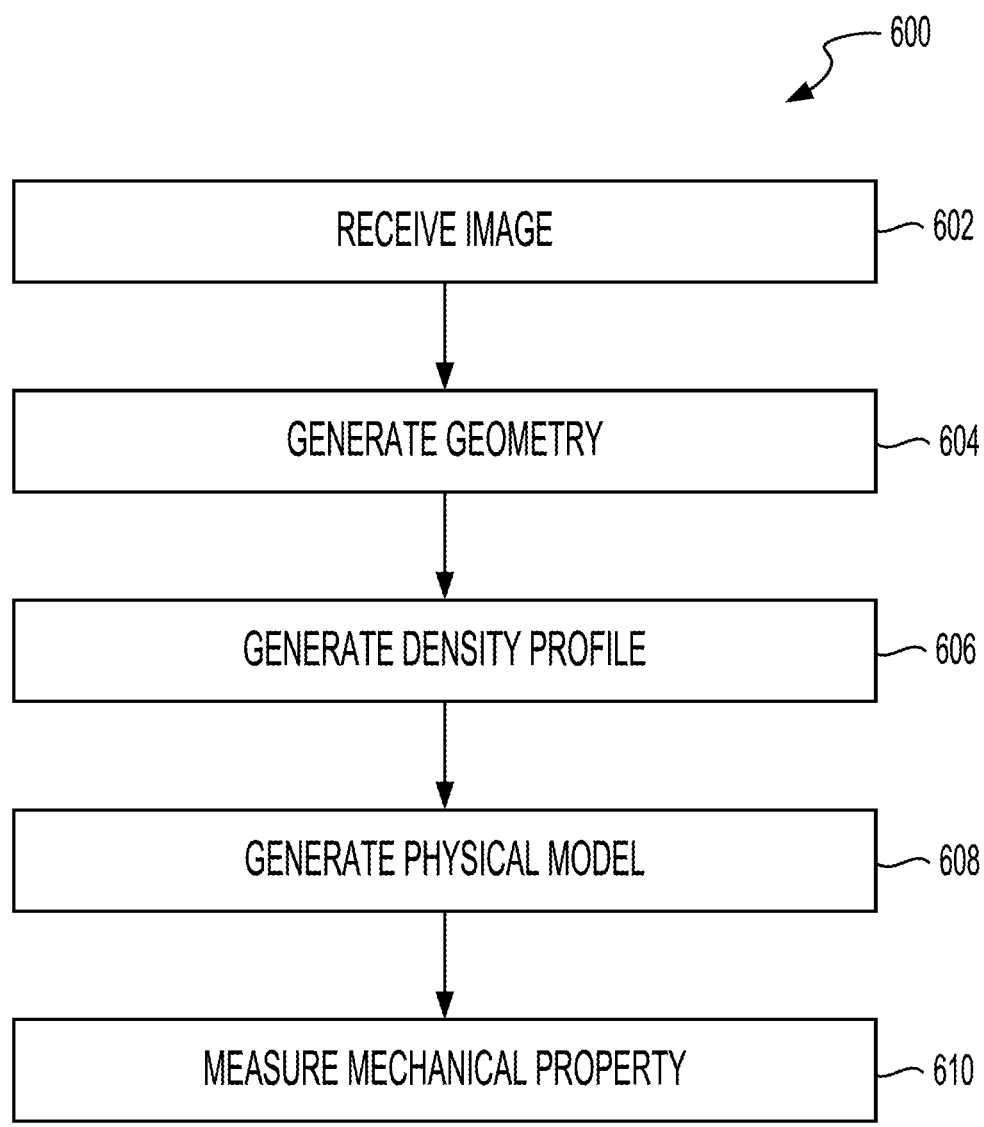
FIG. 6 illustrates a block diagram of an example method of measuring mechanical properties.

FIG. 6 illustrates a block diagram of an example method 600 of measuring mechanical properties. The method 600 can include receiving an image (BLOCK 602). The method 600 can include generating a geometry (BLOCK 604). The method 600 can include generating a density profile (BLOCK 606). The method 600 can include generating a physical model (BLOCK 608). The method 600 can include measuring a mechanical property of physical model (BLOCK 610).

As set forth above, the method 600 can include receiving an image (BLOCK 602). Also referring to FIG. 1, among others, the controller 114 can receive an image from the imaging device 126. The imaging device 126 can be a CT imaging device. The controller 114 can receive a plurality of images to generate a 3D view of the target anatomy of the subject.

In some implementations, the image can be segmented to identify and extract the target anatomy from the images. For example, the controller 114 can receive the image as a data file that can be a Digital Imaging and Communication in Medicine (DICOM) format. The controller 114 can segment the target anatomy on the basis of a threshold intensity of pixels in the grey-scale 2D image projections (axial, sagittal, and coronal) extracted from the DICOM file. The segmentation masks can be created such that pixels or voxels with the same intensity range can be grouped and assigned to be printed using a single material.

The method 600 can include generating the geometry (BLOCK 604). The controller 114 can convert the segmentation masks in geometries 120, which can be 3D digital models. The geometry 120 can be saved as a stereolithography file. For example, each of the 2D projections generated from the DICOM file can be segmented to identify portions of the projection that include the target anatomy and portions of the projection that do not include the target anatomy. The controller 114 can translate the segmented portion of the projection that includes the target anatomy to a layer of the geometry 120.

The method 600 can include generating a density profile (BLOCK 606). The density profile can indicate, for each layer of the geometry 120, the ratio of each of the components of the resin. The density profile can include a pattern or distribution of the resins within each layer of the physical model 102. The ratio of the different components of the resin can change the stiffness or complains of the layer of the physical model 102. For example, the resin can include two components—a first component can cure to a cross-linked hydrogel (e.g., a compliant material) and a second component can cure to an epoxy (e.g., stiff material). The controller 114 can generate the density profile 122 based on deformation maps 116 that can map the intensity values of the images to ratio materials in the layers of physical model 102. For example, based on the deformation map 116, the controller 114 can map relatively high-intensity pixels in the image from the imaging device 126 to a distribution of resin components in the density profile 122 that is relatively stiff and can map relatively low-intensity pixels or voxels in the image from the imaging device 126 to a distribution of resin components in the density profile 122 that is relatively flexible.

The method 600 can include generating a physical model (BLOCK 608). The bioprinter 124 can 3D print the physical model 102. For example, and referring to FIG. 2, among others, the controller 114 can load the geometry 120 into the bioprinter 124. The bioprinter 124 can generate light of different wavelengths. The different wavelengths can cure different components of the bioprinter's resin. The bioprinter 124 can activate the different wavelengths to cure the different components of the resin based on the geometry 120 and the density profile 122. In some implementations, resin can include particles that are embedded into the physical model 102 when the resin cures.

The method 600 can include measuring a physical property (BLOCK 608). Also referring to FIG. 1, among others, the physical model 102 can be coupled to a fluidic circuit and a pump 104 can pump a fluid from the reservoir 110 and through the physical model 102. In some implementations, the fluid can include particles. The physical model 102 can include one or more sensors 112 and the fluid circuit can include one or more sensors 112. For example, the fluid circuit can include a flow sensor within the interior volume of the physical model 102. The method 600 can include measuring physical properties such as flow rates and pressures within the physical model 102. The controller 114 can detect the position of particles flowing through the fluid and through the physical model 102 to determine the fluid vorticity, energy loss, and particle residence time with the physical model 102.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including," "comprising," "having," "containing," "involving," "characterized by," "characterized in that," and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations, elements, or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A method comprising:
   receiving at least one image of a target anatomy of a subject;
   generating an anatomy geometry of the target anatomy based on segmenting at least one image of the target anatomy;
   generating a density profile based on the anatomy geometry and a mapping between voxel values of at least one image of the target anatomy and a deformation value of the target anatomy;
   generating a physical model of the target anatomy based on the anatomy geometry and the density profile; and
   measuring a value of the physical model or a fluid as the fluid flows through the physical model.

2. The method of claim 1, wherein the fluid comprises a plurality of particles and the method further comprises determining a displacement of the plurality of particles between a first time point and a second time point.

3. The method of claim 2, further comprising determining a flow rate based on the displacement of the plurality of particles between the first time point and the second time point.

4. The method of claim 2, further comprising identifying a vorticity within the fluid based on the displacement of the plurality of particles between the first time point and the second time point.

5. The method of claim 1, wherein the value comprises an energy loss.

6. The method of claim 1, wherein the physical model comprises an electrode on a first face of a wall of the physical model and a conducting medium in contact with a second face of the wall.

7. The method of claim 6, wherein measuring the value further comprises measuring a capacitance of the wall between the electrode on the first face of the wall and the conducting medium.

8. The method of claim 1, further comprising:
   embedding a plurality of particles within at least one wall of the physical model;
   determining a displacement of the plurality of particles between a first time point and a second time point; and
   determining a strain of at least one wall based on the displacement of the plurality of particles.

9. The method of claim 1, wherein the fluid comprises a first plurality of particles and the physical model comprises a second plurality of particles embedded within at least one wall of the physical model and the method further comprises:
   illuminating the first plurality of particles with a first wavelength of light; and
   illuminating the second plurality of particles with a second wavelength of light.

10. The method of claim 1, wherein the density profile comprises a dither pattern indicating a material ratio.

11. The method of claim 1, wherein the value comprises a pressure within the physical model.

12. A system comprising one or more processors and a memory comprising processor executable instructions causing the one or more processors to:
   receive at least one image of a target anatomy of a subject;
   generate an anatomy geometry of the target anatomy based on segmenting at least one image of the target anatomy;
   determine a density profile based on the anatomy geometry and a mapping between voxel values of at least one image of the target anatomy and a deformation value of the target anatomy;
   transmit to a three-dimensional printer a data structure including the anatomy geometry and the density profile to manufacture a physical model of the target anatomy; and
   measure a value of the physical model or a fluid as the fluid flows through the physical model.

13. The system of claim 12, wherein the fluid comprises a plurality of particles and the one or more processors:
   determine a displacement of the plurality of particles between a first time point and a second time point.

14. The system of claim 13, wherein the one or more processors determine a flow rate based on the displacement of the plurality of particles between the first time point and the second time point.

15. The system of claim 13, wherein the one or more processors identify a vorticity within the fluid based on the displacement of the plurality of particles between the first time point and the second time point.

16. The system of claim 12, wherein the value comprises, a particle residence.

17. The system of claim 12, wherein the physical model comprises an electrode on a first face of a wall of the physical model and a conducting medium in contact with a second face of the wall, and wherein the one or more processors determine a capacitance of the wall between the electrode on the first face of the wall and the conducting medium.

18. The system of claim 12, wherein the one or more processors:
   determine a displacement of a plurality of particles embedded within at least one wall of the physical model between a first time point and a second time point; and
   determine a strain of at least one wall based on the displacement of the plurality of particles.

19. The system of claim 12, further comprising a laser to generate a first wavelength of light to illuminate a first plurality of particles and generate a second wavelength of light to illuminate a second plurality of particles with a second wavelength of light.

20. The system of claim 12, wherein the density profile comprises, for each voxel of the anatomy geometry, a dither pattern indicating a material ratio.

* * * * *